United States Patent
Preuss et al.

(10) Patent No.: US 8,349,018 B2
(45) Date of Patent: Jan. 8, 2013

(54) REDUCTION OF THE DEVELOPMENT OF STRIPE WEAR ON INSERTS FOR HIP JOINT PROSTHESES BY MODIFYING THE GEOMETRY OF THE TRANSITION BETWEEN THE FACE AND SPHERICAL RECESS

(75) Inventors: Roman Preuss, Kirchheim/Teck (DE); Thomas Pandorf, Wernau (DE)

(73) Assignee: CeramTec GmbH, Plochingen (DE)

( * ) Notice: Subject to any disclaimer, the term of this patent is extended or adjusted under 35 U.S.C. 154(b) by 85 days.

(21) Appl. No.: 12/526,850

(22) PCT Filed: Feb. 25, 2008

(86) PCT No.: PCT/EP2008/052238
§ 371 (c)(1),
(2), (4) Date: Jan. 27, 2010

(87) PCT Pub. No.: WO2008/102014
PCT Pub. Date: Aug. 28, 2008

(65) Prior Publication Data
US 2010/0161071 A1 Jun. 24, 2010

(30) Foreign Application Priority Data
Feb. 23, 2007 (DE) .......... 10 2007 009 439

(51) Int. Cl.
*A61F 2/32* (2006.01)
(52) U.S. Cl. .................. 623/22.24; 623/22.21
(58) Field of Classification Search ...... 623/22.21–22.39
See application file for complete search history.

(56) References Cited

U.S. PATENT DOCUMENTS

| | | |
|---|---|---|
| 5,658,294 A | 8/1997 | Sederholm |
| 5,725,589 A | 3/1998 | Pfaff et al. |
| 2005/0071015 A1 | 3/2005 | Sekel |

FOREIGN PATENT DOCUMENTS

| | | |
|---|---|---|
| DE | 296 01 522 U1 | 9/1996 |
| FR | 2 551 655 A | 3/1985 |
| WO | WO 95/23566 A | 9/1995 |
| WO | WO 02/087476 A | 11/2002 |

*Primary Examiner* — Thomas J Sweet
*Assistant Examiner* — Matthew Schall
(74) *Attorney, Agent, or Firm* — Fulbright & Jaworski LLP

(57) ABSTRACT

A socket insert of a hip joint prosthesis having a spherical-indentation-shaped recess in which a spherical head of a femur is mounted. The spherical indentation has a run-in zone which ends on one side with a circular arc tangentially in an end face of the socket insert and extends on another side as far as the run-in edge. Between a start of the circular arc with a radius of the length ($R_E$) and the run-in edge of the spherical indentation with the radius of the length ($R_K$) the run-in zone forms a curve, the function of which is continuously differentiated twice at every point.

8 Claims, 1 Drawing Sheet

REDUCTION OF THE DEVELOPMENT OF STRIPE WEAR ON INSERTS FOR HIP JOINT PROSTHESES BY MODIFYING THE GEOMETRY OF THE TRANSITION BETWEEN THE FACE AND SPHERICAL RECESS

This application is a §371 of PCT/EP2008/052238 filed Feb. 25, 2008, and claims priority from DE 10 2007 009 439.8 filed Feb. 23, 2007.

Various materials are used for hip joint prostheses in order to realize a biocompatible mounting with a low rate of wear. In this connection, the so-called hard-on-hard material pairings in accordance with the prior art are best suited for lasting and reliable care of the patient. In the case of these material pairings, both the spherical head on the hip shaft and the socket insert in the hip socket are made of a material that is hard in the technical sense. At present, the material pairings ceramic-on-ceramic and metal-on-metal are applied. Current investigations also point in future to a use of the material pairing ceramic-on-metal.

In the case of persistent high loads on hip joint prostheses, signs of wear occur even when the hard materials that have been mentioned are used. Whilst these admittedly do not result in failure, for example in the breakage of a component in the case of prostheses of ceramic materials, nevertheless they are undesirable. The abrasion that develops with the material pairing metal-on-metal as a result of the friction can be harmful for the human body.

Figure 1:
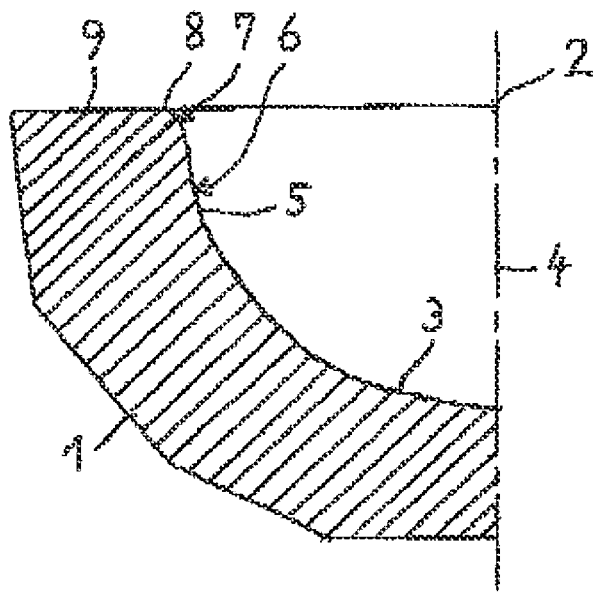

FIG. 1 shows a section through a socket insert 1 made from a ceramic material. The central point 2 of the spherical indentation 3 lies on the axis of symmetry 4 of the spherical indentation. A particular form of wear in the case of hard-on-hard material pairings occurs in the region of the so-called run-in edge 5. This is located at the transition between the spherical indentation 3 of the socket insert 1 and the run-in zone 6. The run-in zone 6 ends with a circular arc 7 tangentially at the transition 8 on the end face 9 of the socket insert 1. As a result of subluxation and also micro-separation of the spherical head that occurs, high loads result, in the region of the run-in edge 5, both for the socket insert 1 and for the spherical head, which is not shown here. Consequently, locally increased wear occurs which, depending on the material, leads to increased abrasion or to a visible increase in surface roughness. The increase in the surface roughness that is referred to as stripe wear is just as undesirable as the metallic abrasion that otherwise occurs to an increased extent.

The increased wear that occurs in the region of the run-in edge 5 is to be attributed to the action of high surface pressure (concentrated load) and also the discontinuous force characteristic during the sliding movement of the spherical head in the region of the run-in zone 6.

The underlying object of the invention is to avoid the wear in the region of the run-in zone or at least reduce it to a great extent.

In order to achieve this object, in accordance with the invention it is proposed that the geometry of the run-in zone 6, between the end point 12 of the circular arc 7 and the run-in edge 5 in the spherical indentation 3 be realized as a curve 14, the function of which can be continuously differentiated twice at every point.

Figure 2:
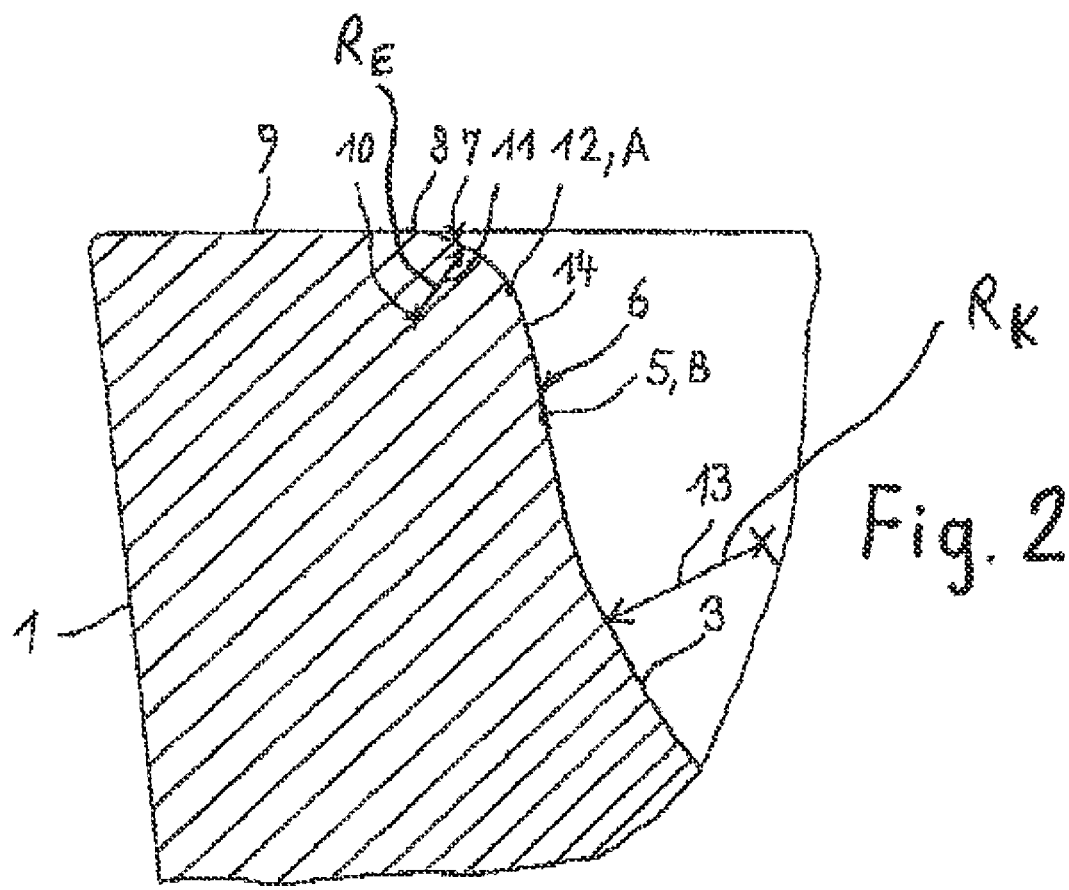

In FIG. 2 the run-in zone 6 in the socket insert 1 is shown as a cutaway portion on an enlarged scale in comparison with that of FIG. 1. The circular arc 7 with the central point 10 at the start of the run-in zone 6 has a radius 11 with the length $R_E$. The circular arc 7 ends at the point 12 where the curve 14 in accordance with the invention of the run-in zone 6 follows on. The transition of the curve 14 to the circular arc of the spherical indentation 3 lies in the run-in edge 5, with the circular arc of the spherical indentation 3 having a radius 13 with the length $R_K$. The point A, the start 12 of the circular arc 7, and the point B, the run-in edge 5, are the points of the curve 14 at which its curvature coincides with the curvature of the respective curve following on, the circular arc 7 and the circular arc 3 of the spherical indentation respectively.

This curve 14 of the run-in zone 6 has at its two end points A and B the respective curvature of the curve that follows on. At the end point A, the formula of the curve 14 thus reads $f''_A(x,y)=1/R_E$ and at the end point B $f''_B(x,y)=1/R_K$.

In this way, the curvature characteristic of the curve 14 on which the spherical head moves between the spherical indentation 3 and the run-in radius 7 is continuous. This results in the charadteristic both of the contact force and also of the surface pressure likewise being continuous. The spherical head rolls off in the socket insert. Sliding movements are avoided.

In order to describe the curve 14 mathematically, various functions are conceivable. For example, at this point the sinusoidal curve shapes known from cam gears or even polynomial forms can be mentioned.

The invention claimed is:

1. A socket insert of a hip joint prosthesis,
    wherein said socket insert has a spherical-indentation-shaped recess;
    wherein the spherical indentation comprises a run-in zone and a run-in edge, wherein said run-in zone ends on one side with a circular arc tangentially in an end face of the socket insert and extends on another side as far as the run-in edge;
    wherein the circular arc has a radius of length ($R_E$) and the run-in edge of the spherical indentation has a radius of length ($R_k$),
    wherein the run-in zone is a curve between a start of the circular arc and the run-in edge of the spherical indentation and
    said curve has a function which is continuously differentiated twice at every point of said curve.

2. A socket insert according to claim 1, wherein the curve at its respective end points (A), the end point of the circular arc, and (B), the run-in edge, has the same curvature as the curves following on from respective end point, the circular arc and the spherical indentation, respectively.

3. A socket insert according to claim 1, wherein the curve has a shape of sinusoidal or has a polynomial form.

4. A socket insert according to claim 2, wherein the curve has a shape of sinusoidal or has a polynomial form.

5. A socket insert according to claim 1, wherein the curve at its end point (A), the start of the circular arc, has a formula of $f''_A(x,y)=1/R_E$ and at its end point (B), the run-in edge and the start of the circular arc of the spherical indentation, has a formula of $f''_B(x,y)=1/R_K$.

6. A socket insert according to claim 2, wherein the curve at its end point (A), the start of the circular arc, has a formula of $f''_A(x,y)=1/R_E$ and at its end point (B), the run-in edge and the start of the circular arc of the spherical indentation, has a formula of $f''_B(x,y)=1/R_K$.

7. A socket insert according to claim 3, wherein the curve at its end point (A), the start of the circular arc, has a formula of $f''_A(x,y)=1/R_E$ and at its end point (B), the run-in edge and the start of the circular arc of the spherical indentation, has a formula of $f''_B(x,y)=1/R_K$.

8. A socket insert according to claim 4, wherein the curve at its end point (A), the start of the circular arc, has a formula of $f''_A(x,y)=1/R_E$ and at its end point (B), the run-in edge and the start of the circular arc of the spherical indentation, has a formula of $f''_B(x,y)=1/R_K$.

* * * * *